United States Patent [19]

Schmitt et al.

[11] 4,116,788

[45] Sep. 26, 1978

[54] PROCESS FOR THE PHOTOPOLYMERIZATION OF ACRYLIC ACID ESTER-CONTAINING COMPOSITIONS

[75] Inventors: Werner Schmitt; Robert Purrmann, both of Starnberg; Peter Jochum, Hechendorf, all of Fed. Rep. of Germany

[73] Assignee: ESPE Fabrik Pharmazeutischer Praparate GmbH, Fed. Rep. of Germany

[21] Appl. No.: 743,323

[22] Filed: Nov. 19, 1976

[30] Foreign Application Priority Data

Nov. 21, 1975 [CH] Switzerland ............... 015138/75
Oct. 14, 1976 [DE] Fed. Rep. of Germany ....... 2646416

[51] Int. Cl.² ........................ C08F 2/46; C08F 4/00
[52] U.S. Cl. ........................ 204/159.23; 204/159.24; 260/42.15; 260/42.52; 260/998.11; 427/54

[58] Field of Search ............. 204/159.18, 159.23, 204/159.24; 260/42.52

[56] References Cited

U.S. PATENT DOCUMENTS

| | | | |
|---|---|---|---|
| 3,699,022 | 10/1972 | Behrens et al. | 204/159.15 |
| 3,814,702 | 6/1974 | Bourdon et al. | 252/426 |
| 3,966,573 | 6/1976 | Bean | 204/159.23 |

*Primary Examiner*—Richard B. Turer
*Attorney, Agent, or Firm*—Burns, Doane, Swecker & Mathis

[57] ABSTRACT

An improved process for the photopolymerization of compositions including photopolymerizable acrylic or methacrylic acid esters and an initiator (e.g., a benzoin compound) is disclosed. The addition of 0.1 to 20 weight percent (based on the amount of polymerizable material) of an organic phosphite substantially reduces the polymerization time of the resulting composition.

10 Claims, No Drawings

PROCESS FOR THE PHOTOPOLYMERIZATION OF ACRYLIC ACID ESTER-CONTAINING COMPOSITIONS

BACKGROUND OF THE INVENTION

Unsaturated ester compounds, such as unsaturated alkyd resins, particularly the esters of acrylic or methacrylic acid, respectively, and especially the acrylates or methacrylates of poly-functional alcohols, are polymerized by means of substances supplying free radicals, particularly by means of organic peroxides.

The radicals introducing this polymerization of the olefinically unsaturated compounds can also develop by means of ultraviolet radiation in combination with so-called ultraviolet initiators or sensitizers when the unsaturated substances to be polymerized contain such initiators and are then subjected to an intensive radiation by means of ultraviolet light. Benzoin or its ether derivatives, respectively, have been used for a long time as particularly suitable ultraviolet initiators for the unsaturated polyester substances. Photopolymerizable dental substances for tooth fillings consisting of a mixture of polyacrylates and acrylic ester monomers and containing benzoin as photoinitiator are described in the British Pat. No. 569,974 (1945). These substances are hardened by means of ultraviolet radiation in the mouth. However, in practice it has been found that the required periods of time for the radiation necessary to achieve polymerization were too long and, therefore, this procedure was not considered of great importance at that time.

The photo-hardening of substances containing polyfunctional acrylic esters is also utilized in other fields. Thus, printing ink or finishing varnish are described in the British Pat. No. 1,198,259 which contain benzoin ethyl ether as ultraviolet initiator and are hardened by means of ultraviolet radiation. Polymer compositions are described in German Offenlegungschrift No. 23, 15, 645 which consist of reaction products of organic isocyanates and hydroxyalkylacrylate and contain unsaturated monomers, such as alkylacrylate or alkylmethacrylate. These substances contain also benzoinalkylether and can be hardened by radiation. In the same way, similar substances are described in the German Offenlegungschrift No. 23, 20, 038 which are utilized in dentistry.

Since unsaturated polyesters often become unstable and tend towards a premature polymerization when the very sensitive polymerization initiators are added so that these substances have then only a short storage time, stabilizers are added to them, e.g. phenolic compounds such as hydroquinone or methoxyphenol. Also organic phosphites, e.g. trimethylphosphite or triphenylphosphite, are disclosed in German Offenlegungschrift No. 19, 34, 637, together with a cuprous salt of an organic acid, for the stabilization of unsaturated polyester substances containing benzoin or its derivatives whereby the phosphite stabilizer should be present in an amount of 200–800 ppm. Ultraviolet-hardenable coloring, impregnating, coating or priming substances based on unsaturated polyesters are described in German Offenlegungschrift No. 21, 04, 958 which contain, besides benzoin ether, also organic esters of the phosphorous acid and organic derivatives of phosphine. In this way, a good storage stability is achieved with a short polymerization speed at the hardening by means of ultraviolet radiation. The utilization of esters of phosphorous acid, e.g., triphenylphosphite, is also described in the German Auslengungschrift No. 10, 98, 712 as an additive to increase the storage and color stability of unsaturated polyester resin substances.

The ultraviolet-initiated hardening of tooth filling substances as well as the sealing of teeth by means of such coating substances has met with great interest in the field of dentistry in the past years. However, so far, either very intensive radiation units must be utilized or long periods of radiation are required in order to obtain a complete hardening. Furthermore, these preparations cannot contain any additives which could effect a discoloring of the polymerized substance after some time under the influence of the environment in the mouth, particularly of the different types of food and liquids. Consequently, the organic phosphine compounds made known, for example, as catalysts of the benzoin-initiated ultraviolet polymerization in the case of the unsaturated polyester substances of German Offenlegungschrift No. 21, 04, 958 cannot be used with dental substances based on acrylic or methacrylic esters because these phosphine compounds lead to a discoloring of the tooth fillings or sealings after a period of time.

SUMMARY OF THE INVENTION

It has now surprisingly been determined that the polymerization of acrylic ester substances, particularly of acrylic or methacrylic esters of poly-functional alcohol compounds, effected by means of benzoin ether and similar ultraviolet initiators can be accelerated by two to ten times by the presence of organic phosphite compounds alone if these organic phosphite compounds are present in a concentration of 0.1 to 20% based on the amount of the ester component. This increase in the sensitivity of the polymerizable acrylic or methacrylic ester substances vis-a-vis ultraviolet radiation is particularly surprising because, according to the status of the art, i.e., in the already mentioned German Offenlegungschrift 19, 34, 637 or in the German Auslegeschrift No. 10, 98, 712, these organic phosphite compounds are added there as stabilizers to prevent premature polymerization of the unsaturated ester substances used therein.

DESCRIPTION OF THE PREFERRED EMBODIMENTS

The aliphatic or aromatic phosphites used as activator for the benzoin-ether-initiated ultraviolet polymerization are preferably utilized in a concentration of 0.1 to 20, preferably 0.1 to 2, most preferably 0.2 to 1, percent by weight based on the amount of the acrylic or methacrylic ester compounds to be polymerized. The benzoin derivatives present as initiators for the ultraviolet polymerization may be present in the customary concentrations, i.e., in an amount of 0.1 to 5%, preferably 0.2 to 2%. Generally, the optimum concentration of the benzoin derivative is 0.2 to 1% (by weight) benzoin derivative, based on the amount of the ester compounds to be polymerized.

The activating organic phosphites can have solely aliphatic or solely aromatic substituents and may also contain both aliphatic and aromatic substituents in the same phosphite compound. In contrast to the system claimed in the German Offenlegungschrift No. 21, 04, 958 in which one of the substituents of the phosphite compound, which is linked to the phosphorus through oxygen, must be aromatic, the phosphites utilized in the present invention may consist of purely aliphatic phosphites. Also, secondary phosphites are very useful, independently of whether the substituents linked to phosphorus through oxygen are aliphatic or aromatic. Examples for the phosphites to be used as activators according to the invention are listed as follows: Dimethyl-phosphite, dioctyl-phosphite, diphenyl-phosphite, tri-i-octyl-phosphite, tri-stearyl-phosphite, trimethyl-phosphite, tri-ethyl-phosphite, tri-i-propyl-phosphite, tris-allyl-phosphite, didecyl-phenyl-phosphite, tri-phenyl-phosphite, tris-4-nonylphenyl-phosphite and tris-4-chlorophenyl-phosphite.

As ultraviolet initiators, benzoin or its derivatives can be used with the substances activated according to the invention, for example, benzoin-methylether, benzoin-ethylether, benzoin-i-propylether, benzoin-butylether, benzoin-trimethylsilylether, α-methylbenzoin, α-methyl-benzoin-methylether, α-methyl-benzoin-trimethylsilylether, α-(2-methoxy-carbonyl-ethyl)-benzoinmethylether, α-(2-cyanethyl)-benzoinmethylether or α-(2-carboxyethyl)-benzoinmethylether.

In this present invention, monomeric acrylates or methacrylates, are utilized as ultraviolet-polymerizable compounds, and in particular the di- or tri-functional acrylic acid or methacrylic acid derivatives which harden to form cross-linked polymers as disclosed, for example, in U.S. Pat. No. 3,066,112 or German Pat. No. 1,921,869. Also, mixtures of these ester compounds can now be easily and rapidly copolymerized and hardened by means of radiation. Examples of methacrylic ester compounds preferably used in the field of dentistry are: 2,2-bis-[p-(α-hydroxy-propoxy-)phenyl]-propane-dimethacrylate (Dimethacrylate I), 2,2,-bis-[p-(β-hydroxy-propoxy-)phenyl]-propane-dimethacrylate (Dimethacrylate II), the reaction product of bisphenol with glycidylmethacrylate (Dimethacrylate III), butandiol-1.4-dimethacrylate, and trimethylolpropanetrimethacrylate.

The essential acceleration of the polymerization and thus of the hardening of the acrylate compounds, particularly of the poly-functional methacrylates mostly used in these compositions, is achieved by means of the new combination of organic phosphites and benzoin derivatives as initiators of the polymerization by radiation with ultraviolet light. With the use of particularly suitable combinations of phosphite and benzoin derivatives, the duration of the polymerization can be shortened by a power of ten with the same radiation intensity and other reaction conditions in comparison with a corresponding substance which, besides the usual additives such as fillers, etc., contains only the respective benzoin derivatives. In this manner, the necessary duration of the radiation can be very much shortened or the desred hardening can be achieved with ultraviolet radiating systems which are simpler and can be built more easily and also require less energy.

The polymerizable substances activated according to the invention can contain the usual fillers although the fillers which can be used should, if possible, be those fillers which practically do not adsorb or adsorb comparatively little ultraviolet light. Pulverized quartz and particularly also barium silicate glasses as well as pulverized polyacrylate are especially suitable. Also quartz or glass fibers can be suitably used as fillers.

Also, the compositions should contain customarily utilized inhibitors to prevent premature, unwanted polymerization of the hardenable substances in order to obtain ready preparations which are stable for storage purposes. Hydroquinone, ionol, methoxyphenol and other conventional inhibitors are suitable in this instance.

The present invention is particularly useful in the field of dentistry because quick hardening is especially desirable. The polymerizable acrylate and methacrylate-based compounds are suitable as tooth fillers as well as coatings for the sealing of teeth or as fixing preparations, particularly for orthodontics. However, it is quite obvious to one skilled in the art that the advantages of the rapid acceleration of polymerization is also of great economic importance in other technical fields where these acrylic or methacrylic ester substances are hardened by ultraviolet radiation, for example, when used as binding agent for printing ink, film coatings on all kinds of objects, etc.

In order to initiate the polymerization, it is sufficient to use the natural sun light as radiation source in view of the increased radiation sensitivity of the combination according to the present invention. However, depending on the field of application, special ultraviolet lamps will preferably be utilized, the emission of which should be within the range from 200 to 400 nm, particularly within the range from 320 to 400 nm, as this is also the case of the known ultraviolet polymerizations which are benzoin-activated.

The invention is additionally illustrated in connection with the following Examples which are to be considered as illustrative of the present invention. It should be understood, however, that the invention is not limited to the specific details of the Examples.

EXAMPLES

Photopolymerization was effected, in each of the Examples, in the following manner:

A white plastic ring with an inner diameter of 7 mm and a height of 2 mm, which is placed on a cover glass of an object support, is filled to its edge without forming bubbles with an ultraviolet-polymerizable compound containing benzoin and/or an α-C and/or O-substituted benzoin derivative as ultraviolet sensitizer or a mixture of one of the mentioned benzoins and one of the listed phosphorous acid esters or with a mixture of a filler (for example, quartz, Li-Al-silicates, Ba-silicates) and an ultraviolet-polymerizable compound which contains one of the mentioned benzoin derivatives or a mixture of one of the mentioned benzoin derivatives and one of the listed phosphorous acid esters and is then covered up with a cover glass of an object support. The specific compositions tested are described below in the Examples. In each instance, the percents by weight of the phosphite compound and the benzoin compound are based on the weight of the ultraviolet polymerizable acrylic or methacrylic ester utilized. A Nuva-Lite (Hg high-pressure lamp made by Caulk) served in each case as the source of light for the photo-polymerization which lamp emits light of the wave length $\lambda > 350$ nm, preferably $\lambda = 366$ nm.

The flat end of the quartz rod of the Nuva-Lite serving as light conductor is placed centrally and planely on the upper glass on the object support for the polymerization and the closed-in ultraviolet-polymerizable substance is polymerized from one side through the cover glass. Polymerization time, $t_2$ (sec.), as used herein is that time after which, when the cover glasses were removed, the rear of the 2 mm thick layer did not permit penetration with a probe at a bearing pressure of 100 g.

EXAMPLE 1

In accordance with the above-described method, the polymerization time $t_2$ (sec.) of Dimethacrylate I (2,2-bis-[p-(γ-hydroxy-propoxy-)phenyl]-propane-dimethacrylate), which was stabilized by means of 200 ppm p-methoxy-phenol and 200 ppm ionol and contained 2.0 percent by weight to 4 percent by weight benzoinmethylether as sensitizer, was determined in the absence of an organic phosphite as well as in the presence of 5 percent by weight tris-4-nonyl-phenyl-phosphite.

| Percent by weight Benzoin-methylether | $t_2$ (sec.) without phosphite | 5 percent by weight tris-4-nonyl-phenyl-phosphite |
|---|---|---|
| 2.0 | 22 | 11 |
| 4.0 | 54 | 26 |

It may be seen that the addition of the phosphite compound substantially reduced the polymerization time of the composition.

EXAMPLES 2 to 7

Similar to Example 1, the polymerization times $t_2$ (sec.) of the ultraviolet polymerization, sensitized by amounts of 0.5 percent by weight benzoin-methylether, of Dimethacrylate I were measured in the presence of different organic phosphites in amounts of 5 percent by weight.

| Ex. | Phosphite | | $t_2$ (sec.) |
|---|---|---|---|
|  | without phosphite | | 9 |
| 2 | tri-phenyl-phosphite | 5 percent by weight | 3 |
| 3 | di-decyl-phenyl-phosphite | " | 4 |
| 4 | tris-allyl-phosphite | " | 3 |
| 5 | tris-i-propyl-phosphite | " | 5 |
| 6 | tri-ethyl-phosphite | " | 3 |
| 7 | tri-methyl-phosphite | " | 3 |

Again, the addition of each of the phosphite compounds substantially reduced the polymerization time of the composition.

EXAMPLES 8 to 15

In accordance with the general procedure as explained above, the polymerization times $t_2$ (sec.) of ultraviolet polymerization of Dimethacrylate I, sensitized by amounts of 0.5 percent by weight of different benzoin derivatives, were determined in the presence of 5 percent by weight di-decyl-phenyl-phosphite.

| | | $t_2$ (sec.) | |
|---|---|---|---|
| Example | Benzoin derivative 0.5 percent by weight | without phosphite | with 5 percent by weight di-decyl-phenyl-phosphite |
| 8 | Benzoin | 20 | 3 |
| 9 | Benzoin-ethylether | 10 | 4 |
| 10 | Benzoin-i-propylether | 10 | 4 |
| 11 | Benzoin-butylether | 18 | 4 |
| 12 | Benzoin-trimethyl-silylether | 11 | 3 |
| 13 | α-methyl-benzoin | 18 | 4 |
| 14 | α-methyl-benzoin-tri-methylether | 17 | 5 |
| 15 | α-methyl-benzoin-methylether | 15 | 3 |

It will again be noted that the addition of the phosphite compound substantially reduced the polymerization time of the compositions including the varying benzoin compounds.

EXAMPLE 16 to 23

The Examples 16 to 23 describe ultraviolet polymerization of Dimethacrylate I in the presence of 5% triethyl-phosphite in each case which compositions were sensitized in each case by 0.5 percent by weight of one of the mentioned benzoin derivatives. The percent by weight refers to the ultraviolet-polymerizable compound. The polymerization time $t_2$ (sec.) was determined as a comparison figure.

| | | $t_2$ (sec.) | |
|---|---|---|---|
| Example | Benzoin derivative 0.5 percent by weight | without phosphite | with 5 percent by weight tri-ethyl-phosphite |
| 16 | Benzoin | 20 | 4 |
| 17 | Benzoin-ethylether | 10 | 2 |
| 18 | Benzoin-i-propylether | 10 | 3 |
| 19 | Benzoin-butylether | 18 | 4 |
| 20 | Benzoin-trimethyl-silylether | 11 | 3 |
| 21 | α-methyl-benzoin | 18 | 3 |
| 22 | α-methyl-benzoin-tri-methylsilylether | 17 | 4 |
| 23 | α-methyl-benzoin-methylether | 15 | 3 |

The improvement in polymerization times utilizing the present invention is again apparent.

EXAMPLE 24

The influence of the utilized amount of phosphite on the polymerization time $t_2$ of the photo-polymerization of Dimethacrylate I sensitized by 4 percent by weight of benzoin-methylether and either 1 or 5 weight percent di-decyl-phenyl-phosphite can be seen from the following Table. The determination of the polymerization times $t_2$ was effected in accordance with the above-described procedure.

| $t_2$ (sec.) | | |
|---|---|---|
| without phosphite | 1 percent by weight of di-decyl-phenyl-phosphite | 5 percent by weight of di-decyl-phenyl-phosphite |
| 54 | 25 | 20 |

EXAMPLES 25 to 28

In accordance with the previously described general procedure, the polymerization times $t_2$ of the ultraviolet polymerization of dimethacrylate II (2,2-bis-[p-(β-hydroxy-propoxy-)phenyl]-propane-Dimethacrylate) sensitized by 0.5 percent by weight of benzoin-methylether were determined in the absence of an organic phosphite as well as with the use of 5 percent by weight of triethyl-phosphite. The polymerization times $t_2$ for the photo-polymerization of butandiol-1.4-dimethacrylate and trimethylolpropanetrimethacrylate were measured in a similar manner with the sensitizing by means of 0.5 percent by weight of different benzoin derivatives in the absence and presence of 1 percent by weight of different organo-phosphites.

| Example | Ultraviolet-poly-merizable compound | Benzoin derivative 0.5 percent by weight | Phosphite | $t_2$(sec.) |
|---|---|---|---|---|
| 25 | Dimethylacrylate II " | Benzoin-methylether " | — Tri-ethyl-phosphite 5 percent by weight | 10 4 |
| 26 | Butandiol-1.4-di-methacrylate " | Benzoin " | — Tri-ethyl-phosphite 1 percent by weight | 75 40 |
| 27 | Trimethylolpropane-trimethacrylate " | Benzoin-methylether " | — Di-decyl-phenyl-phosphite 1 percent by weight | 18 5 |
| 28 | Trimethylolpropane-trimethacrylate " | Benzoin-methylether " | — Tri-ethyl-phosphite 1 percent by weight | 18 3 |

Again, the improvement in polymerization times using the present invention is quite apparent.

EXAMPLES 29 to 40

The accleration, according to the invention, of the polymerization of Dimethacrylate I effected by ultraviolet light can be taken from the table below with variations of benzoin derivatives and types of phosphites. The determination of the polymerization time $t_2$ was effected according to the procedure described in the introduction.

EXAMPLE 41

The accleration of the ultraviolet polymerization of dimethacrylate I by means of a primary phosphite can be noticed from this Example; for reasons of stability, this primary phosphite was used in the form of tetrabutyl-ammonium(TBA-)-salt.

| Ex. | Benzoin derivative (percent by weight) | Phosphite (percent by weight) | $t_2$(sec.) |
|---|---|---|---|
| 41 | Benzoin (0.5) " | — Monooctylphosphite (TBA-salt) (0.5) | 20 8 |

| Example | Benzoin derivatives (percent by weight) | Phosphite(percent by weight) | $t_2$ (sec.) |
|---|---|---|---|
| 29 | Benzoin (0.5) " | — Dioctyl-phosphite (0.5) | 20 10 |
| 30 | α-methyl-benzoin (0.5) " | — Dioctyl-phosphite (0.5) | 18 6 |
| 31 | Benzoin-methylether (0.5) " " | — Dimethyl-phosphite (0.5) Diphenyl-phosphite (0.5) | 9 3 5 |
| 32 | Benzoin-trimethylsilyl-ether (0.5) " | — Dimethyl-phosphite (0.5) | 11 5 |
| 33 | α-(2-methoxycarbonylethyl)-benzoinmethylether (3) " | — Dimethyl-phosphite (0.5) | 13 5 |
| 34 | α-(2-cyanethyl)-benzoin-methylether (3) " | — Dioctyl-phosphite (0.5) | 14 5 |
| 35 | α-(2-carboxyethyl)-benzoin-methylether (3) " | — Diphenyl-phosphite (0.5) | 13 4 |
| 36 | Benzoin-methylether (0.5) " " " | — Tris-β-chloroethyl-phosphite (0.5) Tris-i-octyl-phosphite (0.5) Tristearyl-phosphite (0.5) | 9 2 4 4 |
| 37 | Trigonal 14* (3) " | — Di-decyl-phenyl-phosphite (0.5) | 25 15 |
| 38 | α-(2-methoxycarbonylethyl)-benzoinmethylether (3) " | — Di-decyl-phenyl-phosphite (0.5) | 13 5 |
| 39 | α-(2-cyanethyl)-benzoin-methylether (3) " | — Di-decyl-phenyl-phosphite (0.5) | 14 7 |
| 40 | α-(2-carboxyethyl)-benzoin-methylether (3) " | — Di-decyl-phenyl-phosphite (0.5) | 13 6 |

*Trigonal 14 is a 1:1 mixture of benzoin-isopropylether and benzoin-n-butylether

EXAMPLES 42 to 45

Similar to the Examples 1 to 25, the polymerization time $t_2$ of the ultraviolet polymerization of a mixture consisting of a bi-functional methacrylic ester and an inactive inorganic filler (or filler mixture), such as quartz and/or Li-Al-silicates and/or Ba-silicates, sensitized by benzoin and/or an α-C and/or O-substituted benzoin, is also considerably shortened by adding organophosphites. In this instance, the weight of the filler can amount to many times the weight of the ultraviolet-polymerizable compound.

The polymerization times $t_2$ of the ultraviolet polymerization, sensitized by 1 part by weight of benzoin-methylether, of pastes consisting of 100 parts by weight of Dimethacrylate I and 400 parts by weight of quartz, in the absence and presence of different organic phosphorous acid esters in amounts of 0.4 part by weight, are given below. The indications in weight refer to the photo-polymerizable compound.

| Example | Phosphite (percent by weight) | | $t_2$ (sec.) |
|---|---|---|---|
|  | without phosphite |  | 20 |
| 42 | Tri-phenyl-phosphite | (0.4) | 10 |
| 43 | Di-decyl-phenyl-phosphite | (0.4) | 5 |
| 44 | Tris-4-nonylphenyl-phosphite | (0.4) | 10 |
| 45 | Tris-4-chlorphenyl-phosphite | (0.4) | 4 |

This Example shows that the suprising reduction in polymerization time is achieved when the composition contains substantial amounts of inert filler.

EXAMPLES 46 to 48

In these Examples, the polymerization times $t_2$ of the photopolymerization, sensitized by means of 0.5 percent by weight of different substituted benzoins, of mixtures of silanized and toothlike colored quartz and Dimethacrylate I, which was stabilized by means of 200 ppm p-methoxyphenol and 200 ppm ionol, were determined in accordance with the above described, general method in the absence and in the presence of 5 percent by weight of different organophosphites. The indications in weight refer to the photo-polymerizable compound.

EXAMPLE 49

The reduction of the polymerization time $t_2$, which is observed with the photo-polymerization, sensitized by means of 0.25 part by weight of benzoin-methylether, of a mixture of 370 parts by weight of silanized and colored quartz and 100 parts by weight of Dimethacrylate I in dependence of the amount of the used di-decylphenyl-phosphite, is much more pronounced than in the case of the sensitized ultraviolet polymerization of dimethacrylate I in the absence of a filler (see Example 24). The determination of the polymerization time $t_2$ was effected according to the general method described above.

|  | $t_2$ (sec.) | | |
|---|---|---|---|
|  |  | di-decyl-phenyl-phosphite | |
| Benzoin-methyl ether | without phosphite | 1 part by weight | 5 parts by weight |
| 0.25 part by weight | 30 | 9 | 5 |

EXAMPLES 50 and 51

These Examples describe the reduction of the polymerization time $t_2$ of two commercially available dental preparations A and B which have been sensitized with 0.5 percent by weight of benzoinmethylether by adding 5 percent by weight of didecylphenyl-phosphite according to the invention. The preparation A is available on the market under the commercial name of "Nuva Fil" and is made in accordance with German Offenslegungsschrift No. 21, 26, 419 and contains Dimethacrylate III (the reaction product of bisphenol with glycidylmethacrylate). The preparation B, which is on the market under the commercial name of "Alpha Fil", contains a methacrylic ester obtained by reaction with an aliphatic di-isocyanate according to German Offenlegungsschrift No. 23, 15, 645. The indications in weight refer to the portion of the preparation not containing a filler. The measuring of the polymerization times was effected according to the described general method.

| Example | Benzoin derivative (0.5% by weight) | Phosphite 5% by weight | Quartz % by weight | $t_2$ (sec.) |
|---|---|---|---|---|
|  | Benzoin | — | 400 | 80 |
| 46 | " | Tris-4-nonylphenyl-phosphite | 400 | 9 |
|  | α-methyl-benzoin | — | 400 | 45 |
| 47 | " | Triphenyl-phosphite | 400 | 12 |
|  | α-methyl-benzoin-tri | — | 370 | 46 |
| 48 | methylsilylether " | Di-decyl-phenyl-phosphite | 370 | 7 |

| Example | Preparation | Filler | Benzoin derivative (0.5% by weight) | Phosphite (5% by weight) | $t_2$ (sec.) |
|---|---|---|---|---|---|
| 50 | A (Nuva-Fil) " | Li-Al-silicate glass " | Benzoin-methyl-ether " | — Di-decyl-phenyl-phosphite | 65 30 |
|  | B | Ba-silicate- | Benzoin-methyl- |  |  |

-continued

| Example | Preparation | Filler | Benzoin derivative (0.5% by weight) | Phosphite (5% by weight) | $t_2$ (sec.) |
|---|---|---|---|---|---|
| 51 | (Alpha-Fil) | glass | ether | — | 65 |
|  | "  | "  | "  | Di-decyl-phenyl-phosphite | 35 |

EXAMPLES 52 and 53

In the case of those two Examples, the polymerization times $t_2$ (sec.) and the dark storage stabilities (days) of two mixtures consisting of 100 parts by weight each of Dimethylacrylate I (stabilized by means of 200 ppm p-methoxyphenol, 200 ppm ionol), 390 parts by weight of quartz (silanized and colored) and 1 part by weight of benzoinmethylether are compared to which the following substances had been added:

Mixture C: 0.4 part by weight of triphenyl-phosphite
Mixture D: 0.4 part by weight of triphenyl-phosphite + 0.4 part by weight of triphenyl-phosphine.

The amounts of the weights refer to ultraviolet-polymerizable compound. The determination of the polymerization time was effected in accordance with the indicated general method. In order to determine the dark storage stability, the mixtures were stored under the exclusion of light at different temperatures exposed to the air in a layer thickness of 6 mm and the penetration depth of a probe with a bearing pressure of 100 g was continuously tested. The point of time when the penetration depth amounted for the first time to 5 mm or less was considered as the commencement of the polymerization.

| Ex. | Mixture | $t_2$ (sec.) | Stability in the dark (days) | | |
|---|---|---|---|---|---|
|  |  |  | Room temperature | 36° C | 50° C |
| 52 | C | 10 | >60 | 25 | 19 |
| 53 | D | 10 | 20 | 13 | 13 |

Besides the clearly reduced dark storage stability of mixture D in comparison with mixture C, a pronounced yellow coloring was observed in the case of mixture D after a 14-day storage in water at 36° C. in the polymerized condition (effected in accordance with the indicated general method). This did not occur in the case of mixture C.

EXAMPLE 54

In this Example, the photochemical copolymerization of a mixture consisting of a bi-functional and monofunctional methacrylic ester is effected. The Dimethacrylate I (stabilized by means of 200 ppm p-methoxyphenol and 200 ppm ionol) and methacrylic acid - methylester are mixed in a ratio by weight of 7:3 and sensitized with 0.5% benzoin in the absence as well as in the presence of 5 percent by weight of tri-ethyl-phosphite and then polymerized by means of ultraviolet light. The measuring dimension was the polymerization time $t_2$ which was determined in accordance with the general, described method.

With sensitizing exclusively by means of 0.5 percent by weight of benzoin, a polymerization time $t_2 = 75$ seconds was measured, in the case of a sensitization by means of 0.5 percent by weight of benzoin and 5 percent by weight of tri-ethyl-phosphite, a polymerization time $t_2 = 35$ seconds was measured.

COMPARATIVE EXAMPLE

In order to prove that the polymerization time of the ultraviolet polymerization, sensitized by means of benzoin or a benzoin derivative, of the customary unsaturated polyester resins, which do not represent acrylic esters, cannot be shortened by adding an organic phosphorous acid ester, the polymerization time $t_2$ of a highly reactive unsaturated polyester resin (alkyd based), containing 34 percent by weight of styrol and being commercially available under the name of "Alpolit UP 303" (Manufacturer- Hoechst AG), was determined in accordance with the described general method. The sensitization was effected by means of 0.5 percent by weight of benzoin-methylether in the absence and in the presence of 1 percent by weight of didecylphenyl-phosphite.

|  | $t_2$ (sec.) | |
|---|---|---|
| Benzoin-methylether | without phosphite | 1% by weight of didecylphenyl-phosphite |
| 0.5% by weight | 20 | 20 |

In contrast to the Examples according to the invention, the ultraviolet polymerization cannot be influenced in the case of these polyester substances by means of the combination with phosphite.

Whether an inhibiting effect and thus an improvement of the storage stability, as it is made known in the already mentioned German Offenlegungsschrift No. 19, 34, 637 as well as German Auslegungschrift No. 1, 098, 712, is effected in the case of this substance when adding phosphite, has not been tested since the present invention concerns the opposite effect, i.e., the acceleration of the polymerization by adding phosphite.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a photopolymerizable composition wherein said photopolymerizable portion consists essentially of at least one photopolymerizable ester comprising a di- or tri-functional acrylic or methacrylic acid ester and a benzoin compound photopolymerization activator, the improvement comprising including in said composition from about 0.1 to about 20 percent by weight of the photopolymerizable ester of an organic phosphite photopolymerization activator.

2. The photopolymerizable composition of claim 1 wherein the organic phosphite photopolymerization activator is present in an amount of 0.1 to 2 percent by weight of the photopolymerizable ester.

3. The photopolymerizable composition of claim 2 wherein the organic phosphite photopolymerization activator is present in an amount of 0.2 to 1 percent by weight of the photopolymerizable ester.

4. The photopolymerizable composition of claim 1 wherein the organic phosphite is an aromatic phosphite.

5. The photopolymerizable composition of claim 1 wherein the organic phosphite is an aliphatic phosphite.

6. The photopolymerizable composition of claim 1 wherein the organic phosphite contains both aliphatic and aromatic substituents.

7. The photopolymerizable composition of claim 1 wherein the composition further contains an inert filler.

8. The photopolymerizable composition of claim 1 wherein the composition furher contains a stabilizer.

9. The photopolymerizable composition of claim 1 wherein said composition additionally contains a monofunctional acrylic or methacrylic acid ester.

10. The photopolymerizable composition of claim 1 wherein the benzoin compound is present in an amount of 0.1 to 5 percent by weight of the photopolymerizable ester.

* * * * *